(12) United States Patent
Dextradeur et al.

(10) Patent No.: US 7,094,214 B2
(45) Date of Patent: Aug. 22, 2006

(54) SYSTEM AND METHOD FOR CLEARING AN IMPLANTED CATHETER THAT IS CONNECTED TO A SHUNT

(75) Inventors: Alan J. Dextradeur, Franklin, MA (US); Terri Kelcourse Taylor, Marlborough, MA (US); Rainuka Gupta, Cambridge, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 429 days.

(21) Appl. No.: 10/607,692

(22) Filed: Jun. 27, 2003

(65) Prior Publication Data
US 2004/0267186 A1   Dec. 30, 2004

(51) Int. Cl.
A61M 5/00   (2006.01)
(52) U.S. Cl. .......................................... 604/8
(58) Field of Classification Search ............. 604/8–10, 604/264, 19–22, 523, 267, 288.01–288.04; 128/898; 422/1; 607/115, 116, 122, 126; 623/11.11, 23.64, 26.68, 23.7; 606/32, 34, 606/41, 42, 129
See application file for complete search history.

(56) References Cited

U.S. PATENT DOCUMENTS

| | | | |
|---|---|---|---|
| 3,452,757 A | 7/1969 | Ames | |
| 3,863,641 A | 2/1975 | Popa | |
| 5,454,370 A | 10/1995 | Avitall | |
| 5,454,809 A | 10/1995 | Janssen | |
| 5,507,744 A | 4/1996 | Tay et al. | |
| 5,599,345 A | 2/1997 | Edwards et al. | |
| 5,628,733 A | 5/1997 | Zinreich et al. | |
| 5,651,767 A * | 7/1997 | Schulman et al. ............. 604/8 |
| 5,749,914 A * | 5/1998 | Janssen ..................... 607/116 |
| 5,957,922 A | 9/1999 | Imran | |
| 6,059,778 A | 5/2000 | Sherman | |
| 6,210,411 B1 | 4/2001 | Hofmann et al. | |
| 6,477,429 B1 | 11/2002 | Conger et al. | |
| 2003/0009124 A1 | 1/2003 | Lynch et al. | |
| 2003/0135262 A1* | 7/2003 | Dretler et al. ............. 623/1.15 |

OTHER PUBLICATIONS

Ahlberg et al., "Outcome of Shunt Operation on Urinary Incontinence in Normal Pressure Hydrocephalus Predicted by Lumbar Puncture", J. of Neurol, Neuosurg & Psychiatry 1988:51:105-108.
Black et al., "CSF Shunts for Dementia, Incontinence and Gait Disturbance", Clin Neurosurgery, 1985: Chapter 31, 632-651.
Bradley et al., "Marked Cerebrospinal Fluid Void: Indicator of Successful Shunt in Patients with Suspected Normal Pressure Hydrocephalus"; Radiology, Feb. 1991; 459-466.

(Continued)

*Primary Examiner*—Patricia Bianco
(74) *Attorney, Agent, or Firm*—Eugene L. Szczecina, Jr.

(57) ABSTRACT

A shunt has a housing and a base. The base has a first set of electrodes extending across the base. A catheter is connected to the housing. The catheter has a longitudinal length, a proximal end, and a distal end. The catheter has a second set of electrodes extending along the longitudinal length of the catheter. At least two of the electrodes of said first set are electrically connected to two of the electrodes of the second set. The housing including a self sealing, needle penetrable outer housing wall. The system includes a probe assembly that is selectively penetratable through an outer housing wall.

33 Claims, 3 Drawing Sheets

OTHER PUBLICATIONS

Del Bigio, Marc R., M.D., Ph.D., "Hydrocephalus-Induced Changes in the Composition of Cerebrospinal Fluid", Neurosurg, vol. 25, No. 3, 1989, 416-423.

Dippel et al., "Probabilistic Diagnosis of Normal Pressure Hydrocephalus and Other Treatable Cerebral Lesions in Dementia", J. of Neur. Sciences, 119(1993)123-133.

Gufstafson et al., "Recovery in Hydrocephalic Dementia after Shunt Operation", J. of Neurol, Neurosurg & Psychiatry, 1978, 51, 940-947.

Hindfelt et al., "Brain Proteins in Experimental Portal-Systemic Shunting", Acta Neurol. scandinav. 59, 1979, 275-280.

Jack, et al., "MR Findings in Normal Pressure Hydrocephalus: Significance & Comparison with Other Forms of Dementia", J. of Computer Assisted Tomography, II(6): 923-931, Nov./Dec. 1987.

MALM et al., "CSF Monoamine Metabolites, Cholinesterases and Lactate in the Adult Hydrocephalus Syndrome (Normal Pressure Hydrocephalus) related to CSF hydrodynamic paratmeters"J. of Neurol, Neurosurg & Psychiatry 1991; 54:252-259.

Meyer et al., "Normal Pressure Hydrocephalus; Influences on Cerebral Hernodynamic and Cerebrospinal Fluid Pressure—Chemical Autoregulation", Surg Neurol 1984; 21:195-203.

Pattisapu et al., "Percutaneous Endoscopic Recanilization of the Catheter; a New Technique of Proximal Shunt Revision", Neurosurg, 45:6, Dec. 1999; 1361-1367.

Poca et al., "Shunt Related Changes in Somatostatin, Neuropeptide Y & Corticotropin Releasing Factor Concentrations in Patients with Normal Pressure Hydrocephalus", J Neurol Neurosurg Psychiatry 2001; 70:298-304.

Salmon, James H., M.D.., F.A.C.S., "Senile and Presinile Dementia", Geriatrics, Dec. 1969, 67-72/.

Thomsen et al., "prognosis of Dementia in Normal-pressure Hydrocephalus after a Shunt Operation", Annals of Neurology vol. 20, No. 3, Sep. 1986, 304-310.

Ventureyra et al., "A New Ventricular Catheter for the Prevention and Treatment of Proximal Obstruction in Cebrospinal Fluid Shunts" Neurosurg, vol. 35, No. 5, May 1994, 924-926.

Wikkelso et al., "Dementia of Different Etiologies: Vasoactive Intestinal Polypeptide in CSF", Neurol,35 Apr. 1985, 592-595.

Wikkelso et al., "Neuropeptides in Cerebrospinal Fluid in Normal-Pressure Hydrocephalus and Demential", Eur Neurol 1991; 31:88-93.

Partial European Search Report EP 04253823 dated Sep. 15, 2004.

* cited by examiner

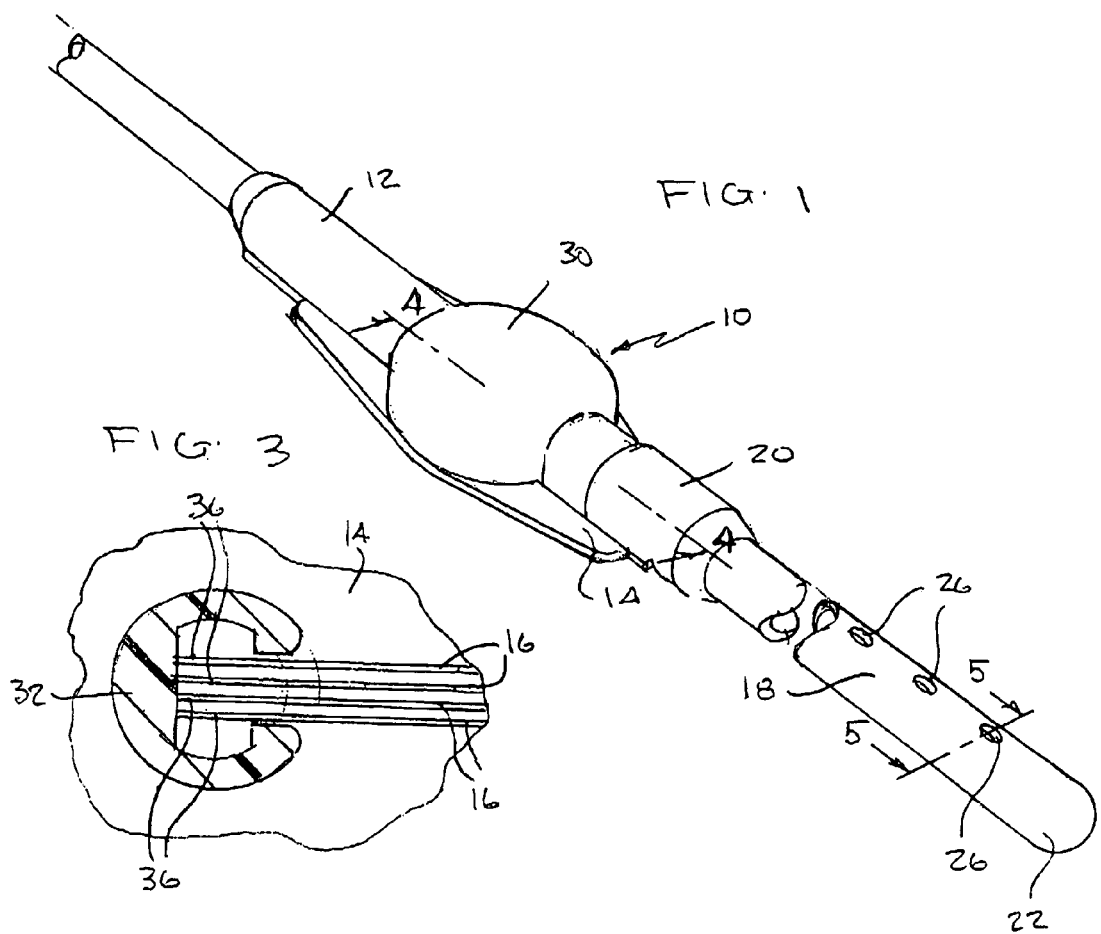
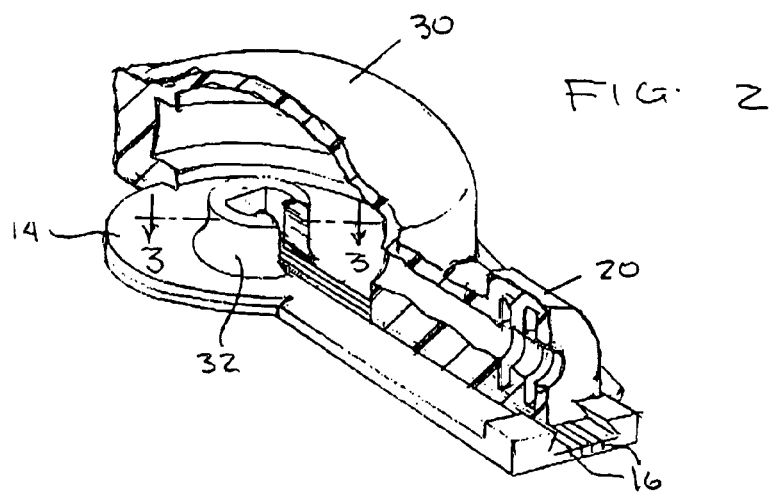

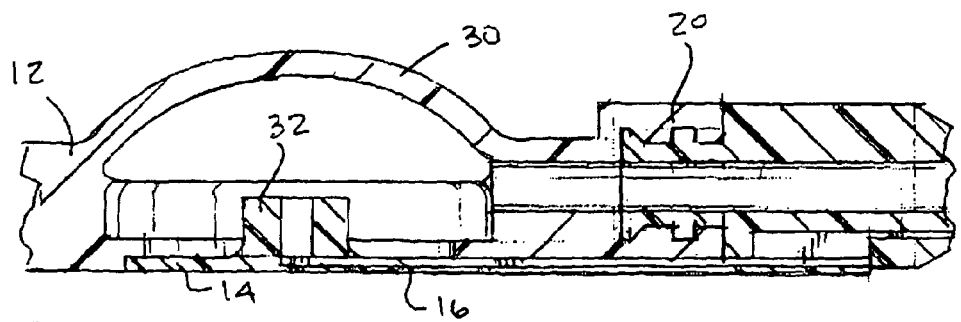
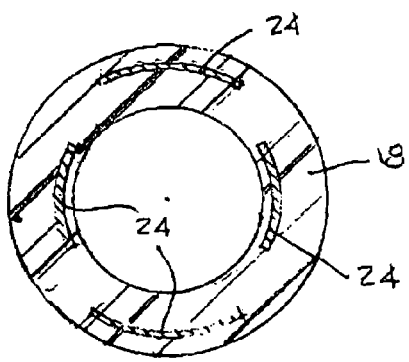
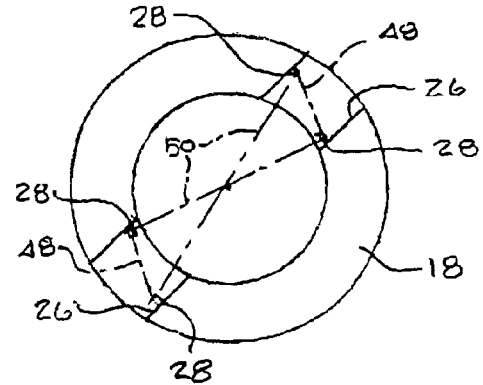
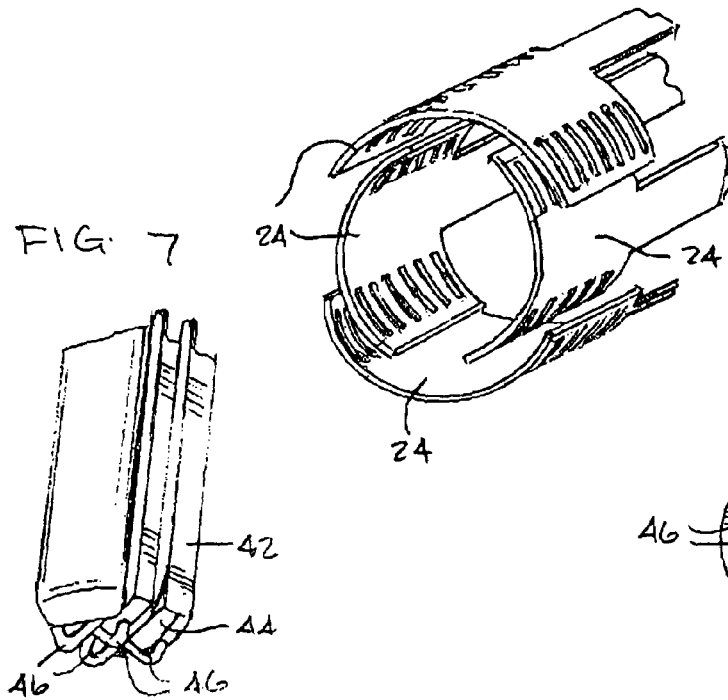
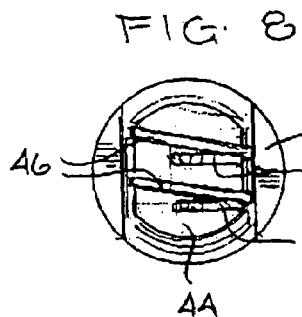

SYSTEM AND METHOD FOR CLEARING AN IMPLANTED CATHETER THAT IS CONNECTED TO A SHUNT

FIELD OF THE INVENTION

The present invention relates generally to a shunt and a catheter having a system for clearing a blockage or obstruction of the catheter apertures.

BACKGROUND OF THE INVENTION

Hydrocephalus is a neurological condition that is caused by the abnormal accumulation of cerebrospinal fluid (CSF) within the ventricles, or cavities, of the brain. CSF is a clear, colorless fluid that is primarily produced by the choroid plexus and surrounds the brain and spinal cord. CSF constantly circulates through the ventricular system of the brain and is ultimately absorbed into the bloodstream. CSF aids in the protection of the brain and spinal cord. Because CSF keeps the brain and spinal cord buoyant, it acts as a protective cushion or "shock absorber" to prevent injuries to the central nervous system.

Hydrocephalus, which affects children and adults, arises when the normal drainage of CSF in the brain is blocked in some way. Such blockage can be caused by a number of factors, including, for example, genetic predisposition, intraventricular or intracranial hemorrhage, infections such as meningitis, head trauma, or the like. Blockage of the flow of CSF consequently creates an imbalance between the amount of CSF produced by the choroid plexus and the rate at which CSF is absorbed into the bloodstream, thereby increasing pressure on the brain, which causes the ventricles to enlarge.

Hydrocephalus is most often treated by surgically inserting a shunt system that diverts the flow of CSF from the ventricle to another area of the body where the CSF can be absorbed as part of the circulatory system. Shunt systems come in a variety of models, and typically share similar functional components. These components include a ventricular catheter which is introduced through a burr hole in the skull and implanted in the patient's ventricle, a drainage catheter that carries the CSF to its ultimate drainage site, and optionally a flow-control mechanism, e.g., shunt valve, that regulates the one-way flow of CSF from the ventricle to the drainage site to maintain normal pressure within the ventricles. The ventricular catheter typically contains multiple holes or apertures positioned along the length of the ventricular catheter to allow the CSF to enter into the shunt system.

Shunting is considered one of the basic neurosurgical procedures, yet it has the highest complication rate. The most common complication with shunting is obstruction of the system. Although obstruction or clogging may occur at any point along the shunt system, it most frequently occurs at the ventricular end of the shunt system. While there are several ways that the ventricular catheter may become blocked or clogged, obstruction is typically caused by growth of tissue, such as the choroid plexus, around the catheter and into the apertures. The apertures of the ventricular catheter can also be obstructed by debris, bacteria, or coagulated blood.

Some of these problems can be treated by backflushing, which is a process that uses the CSF present in the shunt system to remove the obstructing matter. This process can be ineffective, however, due to the small size of the apertures of the ventricular catheter and due to the small amount of flushing liquid available in the shunt system. Other shunt systems have been designed to include a mechanism for flushing the shunt system. For example, some shunt systems include a pumping device within the system which causes fluid in the system to flow with considerable pressure and velocity, thereby flushing the system. As with the process of backflushing, using a built-in mechanism to flush the shunt system can also fail to remove the obstruction due to factors such as the size of the apertures and the degree and extent to which the apertures have been clogged.

Occluded ventricular catheters can also be repaired by cauterizing the catheter to remove blocking tissue, thereby reopening existing apertures that have become occluded. Alternatively, new apertures can be created in the catheter. These repairs, however, may be incapable of removing obstructions from the ventricular catheter depending on the location of the clogged apertures. Additionally, the extent of tissue growth into and around the catheter can also preclude the creation of additional apertures, for example, in situations where the tissue growth covers a substantial portion of the ventricular catheter. Another disadvantage of creating new apertures to repair an occluded ventricular catheter is that this method fails to prevent or reduce the risk of repeated obstructions.

Because attempts at flushing or repairing a blocked ventricular catheter are often futile and ineffective, occlusion is more often treated by replacing the catheter. Although this can be accomplished by removing the obstructed catheter from the ventricle, the growth of the choroid plexus and other tissues around the catheter and into the apertures can hinder removal and replacement of the catheter. Care must be exercised to avoid damage to the choroid plexus, which can cause severe injury to the patient, such as, for example, hemorrhaging. Not only do these procedures pose a significant risk of injury to the patient, they can also be very costly, especially when shunt obstruction is a recurring problem.

Accordingly, there exists a need for a shunt system that minimizes or eliminates the risk of blockage or obstruction of the catheter apertures, and reduces the need for repeated repair and/or replacement.

SUMMARY OF THE INVENTION

The present invention provides a shunt having a housing and a base. The base has a first set of electrodes extending across the base. A catheter is connected to the housing. The catheter has a longitudinal length, a proximal end, and a distal end. The catheter has a second set of electrodes extending along the longitudinal length of the catheter. At least two of the electrodes of said first set are electrically connected to two of the electrodes of the second set.

In another embodiment, the present invention provides a system for clearing an implanted catheter that is connected to a shunt. The system includes a housing having a base. The base has a first set of electrodes extending across the base. The housing including a self sealing, needle penetrable outer housing wall. A catheter is connected to the housing. The catheter has a longitudinal length, a proximal end, and a distal end. The catheter has a second set of electrodes extending along the longitudinal length of the catheter. At least two of the electrodes of the first set are electrically connected to two of the electrodes of the second set. The system includes a probe assembly that is selectively penetratable through the outer housing wall.

In yet another embodiment, the present invention provides a method of clearing an implanted catheter that is connected to a shunt. The method includes the steps of puncturing the outer wall, inserting a probe having a plurality of contacts at a distal end thereof into the socket such that the plurality of contacts contact the first set of electrodes, providing bipolar electrosurgical power to the second set of electrodes via the plurality of contacts and the first set of electrodes, and clearing a fluid blockage in the catheter.

BRIEF DESCRIPTION OF THE DRAWING FIGURES

FIG. 1 is a top perspective view of the shunt according to the present invention;

FIG. 2 is a partial perspective view, with parts broken away, showing the interior of the shunt housing;

FIG. 3 is a cross-sectional view taken along lines 3—3 of FIG. 2 and looking in the direction of the arrows;

FIG. 4 is a cross-sectional view taken along lines 4—4 of FIG. 1 and looking in the direction of the arrows;

FIG. 5 is a cross-sectional view taken along lines 5—5 of FIG. 1 and looking in the direction of the arrows;

FIG. 5A is cross-sectional view similar to FIG. 5, but showing the electrodes partially protruding into an aperature;

FIG. 6 is a partial perspective view of the electrodes;

FIG. 7 is a partial perspective view of the probe;

FIG. 8 is a bottom view of the probe;

DETAILED DESCRIPTION OF THE PRESENT INVENTION

Figure 9:
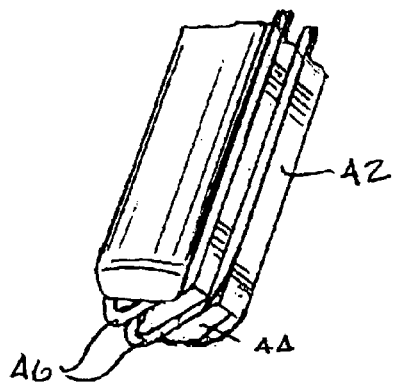
FIG. 9 is a partial perspective view of another embodiment of the probe.

Referring now to FIGS. 1–6, a shunt 10 is illustrated. Shunt 10 includes a housing 12 having a base 14. Base 14 has a first set of electrodes 16 extending across base 14. A catheter 18 is selectively connectable to housing 12. Catheter 18 has a longitudinal length, a proximal end 20, and a distal end 22. Catheter 18 has a second set of electrodes 24 extending along the longitudinal length of the catheter. Each of the electrodes of the first set 16 is electrically connected to a respective one of the electrodes of the second set 24 in a manner known to those skilled in the art. Preferably, the first set of electrodes and the second set of electrodes each include four electrodes.

As illustrated in FIGS. 1 and 4, the catheter proximal end 20 is connected to housing 12. The catheter distal end 22 is disposed remote from housing 12 and has a plurality of apertures 26 adjacent to the distal end to preferably receive cerebrospinal fluid (CSF) when in use. As illustrated in FIG. 5A, a portion 28 of each of the electrodes of the second set 24 extends or projects into at least one of the plurality of apertures 26. Portion 28 is relatively small with respect to the size of aperture 26, so as not to interfere with the normal function of the shunt. At least a first one of the electrodes of the second set 24 extends into a first one of the plurality of apertures 26, and at least a second one of the electrodes of the second set 24 extends into a second one of the plurality of apertures, such that the first one of the plurality of apertures is disposed approximately diametrically opposed to the second one of the plurality of apertures. Thus, the catheter lumen can be cleared when both of these electrodes are activated.

In addition, at least a first one of the electrodes of the second set 24 extends into a first one of the plurality of apertures, and at least a second one of the electrodes of the second set 24 extends into the same first one of the plurality of apertures, but preferably diametrically opposed to the first one of the plurality of electrodes as illustrated in FIG. 5A. Thus, the aperture itself can be cleared when both of these electrodes are activated. Preferably, an electrode projects into each of the apertures, or substantially all of the apertures so that the catheter can be effectively cleared of any blockage.

The shunt housing 12 further includes a self-sealing, needle penetrable outer housing wall 30. Housing 12 further includes a socket 32 for receiving a probe 42. The first set of electrodes 16 extends at least partially through a base of socket 32. The first set of electrodes has a first end 36 that terminate in the base of the socket. Socket 32 is illustrated as having an internal double D-shaped cross-section so that it can only mate with probe 42 in one of two positions. However, the probe and socket can have any correspondingly mating geometric shape to ensure the desired orientation and alignment of the contacts at the distal end of the probe (to be described below) with the respective electrodes of the first set of electrodes.

Figure 10A:
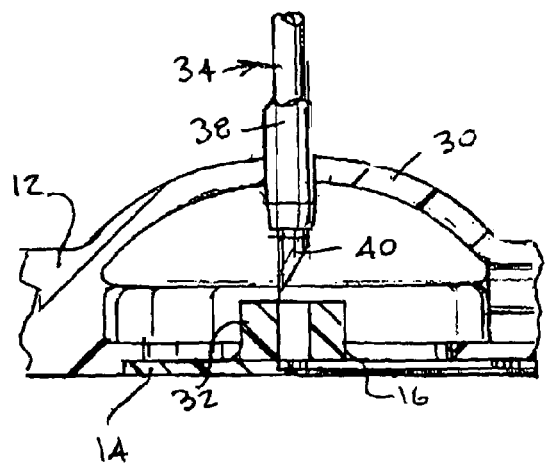
FIG. 10A is a partial cross-sectional view of the shunt housing showing the housing dome being penetrated by a needle and sheath assembly.
Figure 10B:
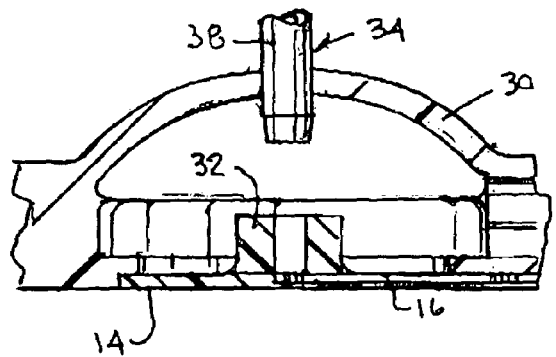
FIG. 10B is a partial cross-sectional view of the shunt housing showing the housing dome being penetrated by the sheath with the needle being withdrawn.
Figure 10C:
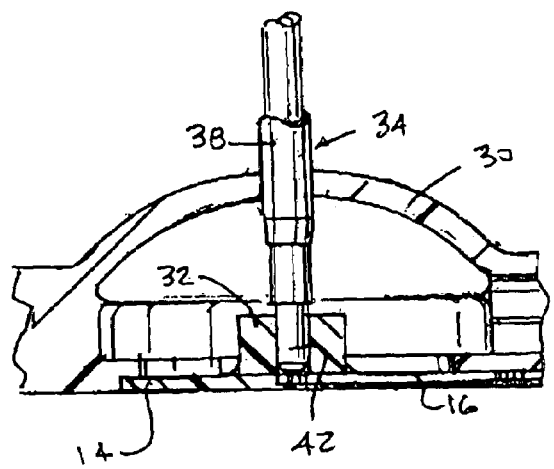
FIG. 10C is a partial cross-sectional view of the shunt housing showing the housing dome being penetrated by the sheath and the probe being inserted into the housing.

As illustrated in FIGS. 10A–10C, the probe assembly 34 is selectively penetrable through the outer housing wall 30, which is preferably dome-shaped. Probe assembly 34 includes a sleeve or sheath 38, a retractable needle 40, and a retractable probe 42. To insert the probe assembly into the housing 12, needle 40, which is within sheath 38, initially penetrates wall 30 until sheath 38 is in sealing contact with wall 30, as illustrated in FIG. 10A. Needle 40 is then withdrawn from sheath 38, as illustrated in FIG. 10B. Probe 42 is then inserted within sheath 38 until the distal end 44 of probe 42 is matingly received within socket 32. As illustrated in FIGS. 7 and 8, the distal end 44 of probe 42 has a four contacts 46, each of which contacts one of the electrodes 16 of the first set of electrodes to close the circuit from the probe assembly to the electrodes in the second set of electrodes. As illustrated in FIG. 9, probe 42 may include only two contacts at its distal end 44. The contacts 46 are preferably resiliently biased in the distal direction to ensure contact with electrodes 16.

Once the probe 42 has been fully inserted into the housing 12 such that the contacts 46 are in contact with the electrodes 16, bipolar electrosurgical power from an electrosurgical generator can then be provided to the second set of electrodes 24 via the plurality of contacts 46 and the first set of electrodes 16. Referring now to FIG. 5A, the bipolar power can be applied to any two of the electrodes 24 such that any two of the four portions 28 are sufficiently charged to cause an arc there across, which can clear a fluid blockage in the catheter 18. For example, the arc can be created across the aperture 26, as illustrated by dashed lines 48, to clear a blockage occurring in the aperture. Additionally, the arc can be created across the catheter lumen, as illustrated by dashed lines 50, to clear a blockage occurring within the lumen. Preferably, both the aperture and the lumen will be charged with bipolar electrosurgical power to ensure that the blockage within the catheter has been cleared. However, depending upon the needs of the surgeon, only selective apertures and/or the lumen may be cleared. One skilled in the art will readily recognize that this can simply be accomplished with appropriate switches connected to the electrosurgical generator.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A shunt comprising:
   a housing having a base, said base having a first set of electrodes extending across said base;
   a catheter being connected to said housing, said catheter having a longitudinal length, a proximal end, and a distal end, said catheter having a second set of electrodes extending along the longitudinal length of the catheter, at least two of said electrodes of said first set being electrically connected to two of said electrodes of said second set.

2. The shunt according to claim 1, wherein said catheter proximal end is connected to said housing, and said catheter distal end is disposed remote from said housing, said catheter having a plurality of apertures adjacent to said distal end.

3. The shunt according to claim 2, wherein a portion of each of said electrodes of said second set extends into at least one of said plurality of apertures.

4. The shunt according to claim 3, wherein at least a first one of said electrodes of said second set extends into a first one of said plurality of apertures, and at least a second one of said electrodes of said second set extends into a second one of said plurality of apertures.

5. The shunt according to claim 4, wherein said first one of said plurality of apertures is disposed approximately diametrically opposed to said second one of said plurality of apertures.

6. The shunt according to claim 3, wherein at least a first one of said electrodes of said second set extends into a first one of said plurality of apertures, and at least a second one of said electrodes of said second set extends into said first one of said plurality of apertures.

7. The shunt according to claim 6, wherein said first one of said electrodes of said second set is disposed approximately diametrically opposed within said first one of said plurality of apertures with respect to said second one of said electrodes of said second set.

8. The shunt according to claim 5, wherein at least a third one of said electrodes of said second set extends into said first one of said plurality of apertures.

9. The shunt according to claim 8, wherein said first one of said electrodes of said second set is disposed approximately diametrically opposed within said second one of said plurality of apertures with respect to said third one of said electrodes of said second set.

10. The shunt according to claim 8, wherein at least a fourth one of said electrodes of said second set extends into said second one of said plurality of apertures.

11. The shunt according to claim 10, wherein said second one of said electrodes of said second set is disposed approximately diametrically opposed within said second one of said plurality of apertures with respect to said fourth one of said electrodes of said second set.

12. The shunt according to claim 3, wherein said housing further includes a self sealing, needle penetrable outer housing wall.

13. The shunt according to claim 12, wherein said housing further includes a socket for receiving a probe.

14. The shunt according to claim 13, wherein said first set of said electrodes extends at least partially through a base of said socket.

15. The shunt according to claim 13, wherein said first set of said electrodes have a first end that terminate in a base of said socket.

16. The shunt according to claim 3, wherein said first set of said electrodes include at least four electrodes, and said second set of said electrodes include at least four electrodes.

17. The shunt according to claim 13, wherein said socket has an internal double D-shaped cross-section.

18. A system for clearing an implanted catheter that is connected to a shunt, said system comprising:
    a housing having a base, said base having a first set of electrodes extending across said base, said housing including a self sealing, needle penetrable outer housing wall;
    a catheter being connected to said housing, said catheter having a longitudinal length, a proximal end, and a distal end, said catheter having a second set of electrodes extending along the longitudinal length of the catheter, at least two of said electrodes of said first set being electrically connected to two of said electrodes of said second set; and
    a probe assembly being selectively penetratable through said outer housing wall.

19. The system according to claim 18, wherein said probe assembly includes a retractable needle for penetrating said outer wall and a sheath disposed about said needle.

20. The system according to claim 19, wherein said probe assembly includes a retractable probe, said probe having a distal end including a plurality of contacts.

21. The system according to claim 20, wherein said plurality of contacts are resiliently biased in said distal direction.

22. The system according to claim 21, wherein said housing further includes a socket for receiving said probe.

23. The system according to claim 22, wherein said first set of said electrodes extends at least partially through a base of said socket.

24. The system according to claim 22, wherein said first set of said electrodes have a first end that terminate in a base of said socket.

25. The system according to claim 20, wherein said first set of said electrodes include at least four electrodes, and said second set of said electrodes include at least four electrodes.

26. The system according to claim 25, wherein said plurality of contacts include at least two contacts.

27. The system according to claim 25, wherein said plurality of contacts include at least four contacts.

28. The system according to claim 22, wherein said socket has an internal double D-shaped cross-section.

29. The system according to claim 28, wherein said probe has an external double D-shaped cross-section that mates with the internal double D-shaped cross-section of said socket.

30. A method of clearing an implanted catheter that is connected to a shunt, wherein said shunt includes a housing having a base, said base having a first set of electrodes extending across said base, said housing including a self sealing, needle penetrable outer housing wall, said housing further includes a socket, and wherein said catheter being connected to said housing, said catheter having a longitudinal length, a proximal end, and a distal end, said catheter having a second set of electrodes extending along the longitudinal length of the catheter, at least two of said electrodes of said first set being electrically connected to two of said electrodes of said second set, said method comprising the steps of:

puncturing said outer wall;

inserting a probe having a plurality of contacts at a distal end thereof into said socket such that said plurality of contacts contact said first set of electrodes;

providing bipolar electrosurgical power to said second set of electrodes via said plurality of contacts and said first set of electrodes; and clearing a fluid blockage in said catheter.

31. The method according to claim 30, wherein said catheter has a plurality of apertures adjacent to said distal end, said providing step includes providing power to two electrodes each having a portion projecting into the same aperture.

32. The method according to claim 30, wherein said catheter has a plurality of apertures adjacent to said distal end, said providing step includes providing power to two electrodes each having a portion projecting into apertures that are approximately diametrically opposed to each other.

33. The method according to claim 30, wherein said catheter has a plurality of apertures adjacent to said distal end, said providing step includes providing power to two electrodes each having a portion projecting into apertures that are approximately diametrically opposed to each other, and includes providing power to two electrodes each having a portion projecting into apertures that are approximately diametrically opposed to each other.

* * * * *